(12) United States Patent
Oxenkrug et al.

(10) Patent No.: US 6,849,654 B2
(45) Date of Patent: Feb. 1, 2005

(54) 5-METHOXY-CARBONYLAMINO-N-ACETYLTRYPTAMINE COMPOUNDS AND DERIVATES THEREOF

(75) Inventors: Gregory F. Oxenkrug, Newton, MA (US); Nikolai S. Zefirov, Moscow (RU); Sergey O. Bachurin, Chernogolovka (RU)

(73) Assignee: Caritas St. Elizabeth's Medical Center of Boston, Inc., Boston, MA (US)

(*) Notice: Subject to any disclaimer, the term of this patent is extended or adjusted under 35 U.S.C. 154(b) by 0 days.

(21) Appl. No.: 10/390,967

(22) Filed: Mar. 18, 2003

(65) Prior Publication Data

US 2003/0176488 A1 Sep. 18, 2003

Related U.S. Application Data

(63) Continuation of application No. 09/834,041, filed on Apr. 12, 2001, now Pat. No. 6,562,858, which is a continuation-in-part of application No. 09/559,609, filed on Apr. 27, 2000, now Pat. No. 6,239,162.
(60) Provisional application No. 60/134,573, filed on May 17, 1999.

(51) Int. Cl.$^7$ .......................................... A61K 31/4045
(52) U.S. Cl. ..................................... 514/415; 514/418
(58) Field of Search ................................ 514/415, 356, 514/418

(56) References Cited

U.S. PATENT DOCUMENTS

4,803,218 A * 2/1989 Stanley et al. ............... 514/414
5,756,507 A * 5/1998 Goulet et al. ................ 514/255
6,011,054 A   1/2000 Oxenkrug et al. ........... 514/415
6,063,805 A   5/2000 Oxenkrug et al. ........... 514/415
6,239,162 B1  5/2001 Oxenkrug .................... 514/415

FOREIGN PATENT DOCUMENTS

| WO | WO 98/44796    | 10/1998 |
| WO | WO 98/44924 A1 | 10/1998 |
| WO | WO 99/23070    | 5/1999  |
| WO | WO 00/12045    | 3/2000  |

OTHER PUBLICATIONS

E. Molinari, et al., "2-[$^{125}$I] Iodo–5methoxycarbonylamino–N–acetyltryptamine: a selective radioligand for the characterization of melatonin $ML_2$ binding sites," *European Journal of Pharmacology*, 301: 159–168, 1996.

E. Molinari, et al., "Localization and Characterization of ML–2 Binding Sites with 2–[$^{125}$I]–MCA–NAT to CNS and Peripheral Tissues of Various Species," *Society for Neuroscience Abstracts*, vol. 20, Abstract No. 479.3, 1994.

M. Mor, et al., "Medicinal Chemistry Feature Molecule—Guest Editor: Matthew J. Dowd—Melatonin," *Current Medicinal Chemistry*, 6:501–518, 1999.

* cited by examiner

*Primary Examiner*—Phyllis Spivack
(74) *Attorney, Agent, or Firm*—Nixon Peabody LLP

(57) ABSTRACT

Compositions comprising 5-methoxy-carbonylamino-N-acetyltryptamine compounds and derivatives thereof for the treatment of depression are disclosed.

7 Claims, 2 Drawing Sheets

5-METHOXY-CARBONYLAMINO-N-ACETYLTRYPTAMINE COMPOUNDS AND DERIVATES THEREOF

CROSS-REFERENCE TO RELATED APPLICATION

This application is a continuation of U.S. Ser. No. 09/834,041 filed on Apr. 12, 2001, now U.S. Pat. No. 6,562,858, the content of which is relied upon and incorporated by reference in its entirety, which is a continuation-in-part of U.S. patent application Ser. No. 09/559,609 filed on Apr. 27, 2000, now U.S. Pat. No. 6,239,162, the content of which is relied upon and incorporated by reference in its entirety, and benefit of priority under 35 USC § 120 in hereby claimed, which claims the benefit of U.S. Provisional Application No. 60/134,573 filed May 17, 1999.

BACKGROUND OF THE INVENTION

1. Field of the Invention

The present invention relates to the method of treatment of depression in a human being identified as having depression. This method comprises the administration of a therapeutically effective depression treatment amount of agonists of melatonin-type 3 receptors (MT-3); 5 MCA-NAT and its analogs. MT-3 agonists may be administered alone or in combination with other agents, e.g. $Ca^{++}$ antagonists.

2. Technical Background

Depression is a difficult mental disorder to treat. Patients having such a disorder are often reluctant to seek the medical attention necessary to diagnose the disorder. Such reluctance is often related to the patient's fear of the stigma associated with seeking psychiatric help or to the patient's feeling of worthlessness associated with depression. Moreover, once the patients seek competent psychiatric help, it is difficult to successfully treat the disorder through psychoanalytic approach alone.

In the Diagnostic and Statistical Manual of Mental disorders, Fourth Edition, (DSM IV published by the American Psychiatric Association, depressive disorders are classified under mood disorders and are divided into three types: major depressive disorder, dysthymic disorder and depressive disorder not otherwise specified. Major depressive disorder and dysthymic disorder are differentiated based on chronicity, severity and persistence. In major depression, the depressed mood must be present for two weeks. In dysthymic disorder, the depressed mood must be present for two weeks. In dysthymic disorder the depressed mood must be present most days over a period of two years. Usually, major depressive disorder is characterized by its sharp contrast to usual functioning. A person with a major depressive episode can be functioning and feeling normal and suddenly develop severe symptoms of depression. By contrast, a person with dysthymic disorder has chronic depression with less severe symptoms than major depression.

In an effort to treat depression, a variety of antidepressant compositions have been developed. Among these are the selective serotonin reuptake inhibitors (SSRI), such as setraline (registered trademark ZOLOFT™—Pfizer), fluoxetine (registered trademark PROZAC™—Eli Lilly), paroxetine (trade name PAXIL™—Smith Kline Beecham), and fluvoxamine (trade name LUVOX™). Other examples of antidepressant compositions include tricyclic antidepressants such as those sold under the registered trademark ELAVIL™ (Merck, Sharpe and Dohme); aminoketone antidepressants such as bupropion; and lithium, a metal used to treat bipolar disorder. However, these drugs are potent, often generating problematic side effects such as lethargy, clouded thinking, a lack of ability to concentrate, and sexual dysfunction. Often, these drugs take about six to eight weeks to exhibit any desirable therapeutic effects. This time period can be prolonged when the correct drug or combinations of drugs has to be determined, by trial and error, before any therapeutic effects are observed. Furthermore, current research is beginning to unveil that many of these drugs produce undesirable physiological side effects (Sipgset, O. *Drug Saf.* 1999. 20(3):277–287; Pache, P. *Curr. Med. Chem.* 1999. 6(6):469–480), and it is also unknown how these drugs may affect pediatric and adolescent patients (Jensen P. S. *Child and Adolescent Research* 1999).

Melatonin (N-acetyl-5-methoxytryptamine) is a natural hormone synthesized and secreted primarily by the pineal gland, with highest levels occurring during the dark period of a circadian light-dark cycle. The hormone is also found in the retina and gut. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology. The inventors have recently observed the antidepressant-like activity of melatonin in the mouse tail suspension test (Prakhie I. V. and G. F. Oxenkrug 1998).

Pharmacological studies have shown that picomolar concentrations of melatonin selectively inhibit the calcium-dependent release of dopamine from rabbit and chicken retina through the activation of a site having the functional and pharmacological characteristics of a receptor. Using the radioligand, 2-[$^{125}$I]iodomelatonin, melatonin receptor sites have been detected in vertebrate retina (Dubocovich, M. L., *Nature*, 306:782–784 (1983); Dubocovich, M. L., *Eur. J. Pharmacol.* 105:193–194 (1984); Dubocovich, M. L., *J. Pharmacol. Exp. Ther.* 234:395–401, (1985)). Melatonin binding sites have been localized primarily in the suprachiasmatic nucleus and pars tuberalis/median eminence of mammals including humans (Reppert et al., *Science* 242:78–81 (1988) and Duncan et al., *Endocrinol.* 125:1011–1018 (1989).

While the radioligand, 2-[$^{125}$I]iodomelatonin, is a useful probe for the localization and characterization of melatonin receptors, a significant problem in further elucidating the mechanism of action of melatonin is the lack of potent and selective melatonin receptor agonists and antagonists. Such agonists/antagonists could find application in not only in the study of melatonin receptor interactions but also in the treatment of conditions, possibly affected by melatonin activity, such as depression, jet-lag, disturbances in the sleep-wakefulness cycle, hypertension, glaucoma, reproduction and neuroendocrine disorders.

Generally, agonists of neurotransmitters and neurohormones are structurally related to the transmitter they mimic, whereas antagonists may be structurally unrelated and quite diverse. To date all of the known melatonin agonists are derivatives of melatonin itself, e.g. 2-iodomelatonin, 6-chloromelatonin, 6,7-dichloro-2-methylmelatonin and 8-hydroxymelatonin, all of which contain the 5-methoxy indole ring as an essential moiety. See, Dubocovich, et al., *Proc. Nat'l. Acad. Sci.* (USA), 84:3916–3918 (1987); Dubocovich, M. L., *J. Pharmacol. Exp. Ther.*, 234:395 (1985); Dubocovich, M. L., *Trends Pharmacol. Sci.*, 16:50–56 (1995).

Membrane associated melatonin sites have recently been classified into mt-1, MT-2 and MT-3 subtypes (Marco et al., 1999), 5-methoxy-carbonylamino-N-acetyltryptamine (5-MCA-NAT), an indole analogue, is an MT-3 agonist (Marco et al., 1999). The physiological function of this putative MT-3 site was unknown.

5-MCA-NAT has been shown to bind with high affinity to MT-3 melatonin sites of hamster brain and shows low affinity or efficacy for other melatonin receptors (Mollinari, E. J. et al., *Soc. Neurosc. Abstr.* 20:1168 (1994)). 5-MCA-NAT is classified as a melatonin receptor agonist.

Therefore, what is needed is an effective, pharmacologically-based treatment for depression. It would further be desirable to have a treatment that potentiates the action and reduces the side effects of known compositions used in the treatment of depression. Such a method of treatment is lacking in the prior art.

SUMMARY OF THE INVENTION

The present invention relates to a method of treating depression, an obsessive compulsive disorder or anxiety in a human in need thereof which comprises administering an effective amount of melatonin receptors (MT-3) agonists: 5-methoxy-carbonylamino-N-acetyltryptamine (5-MCA-NAT) or analogs thereof set forth below as formula I.

The present invention further includes a pharmaceutical composition comprising an analog of formula I and a pharmaceutically acceptable carrier.

DETAILED DESCRIPTION OF THE INVENTION

Figure 1:
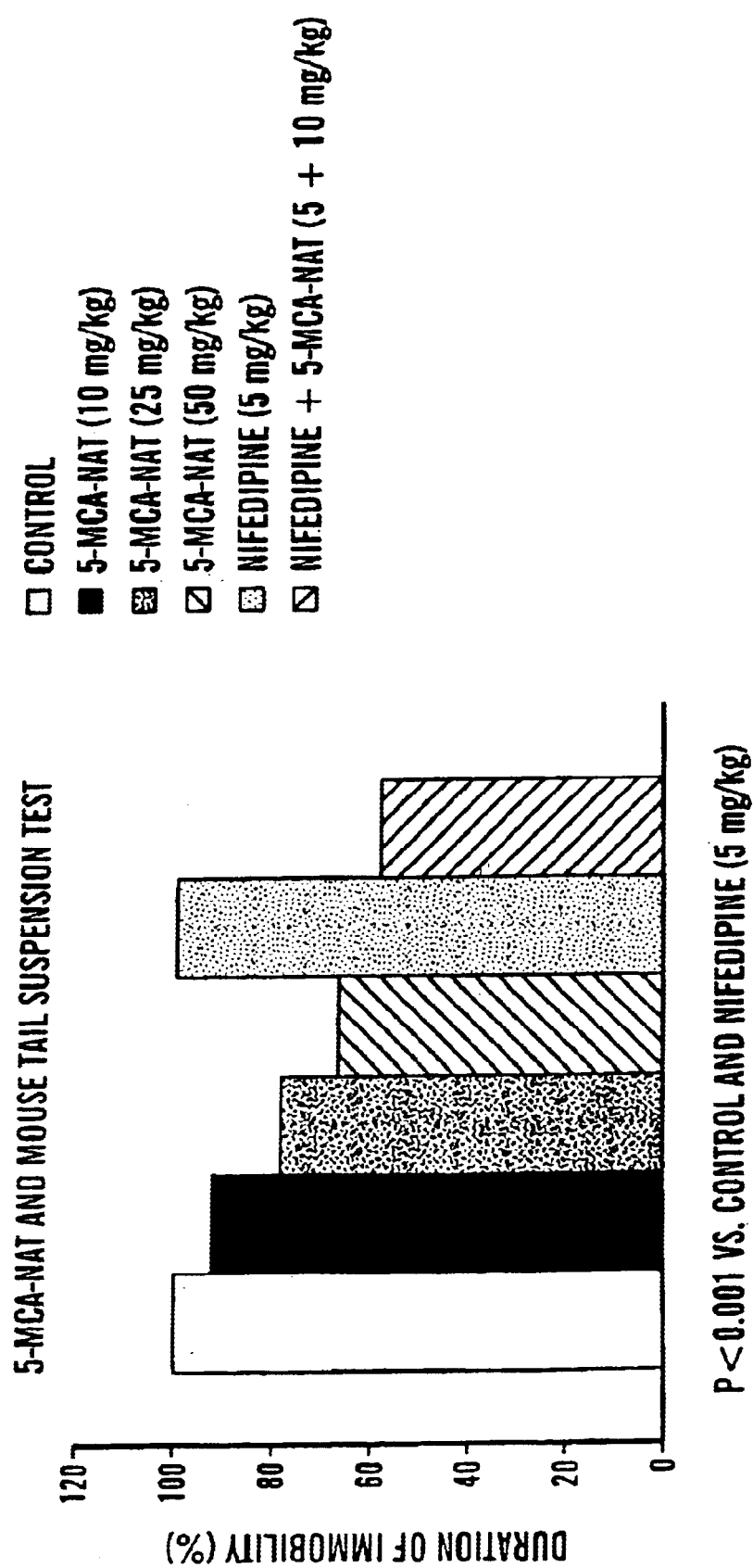
FIG. 1 is a graph showing the results of 5-MCA-NAT in the mouse tail suspension test.

The present invention relates to a method and pharmaceutical composition for treatment of depression in a human being identified as having depression. This method comprises the administration of a therapeutically effective depression treatment amount of MT-3 agonists: methoxy-carbonylamino-N-acetyltryptamine (5-MCA-NAT) or its analogs to a human being identified as having depression. The MT-3 agonists may be administered alone or in combination with other agents, e.g., $Ca^{++}$ antagonists. MT-3 agonists may also be administered in conjunction with a known composition used in the treatment of depression.

In accordance with the present invention, the 5-MCA-NAT analogs have the following formula:

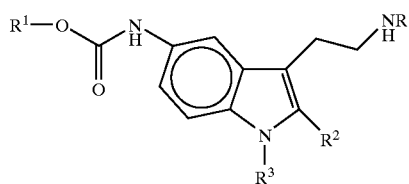

I wherein R is —C(=O)$R^1$, —S(O)2$R^1$ or S(O)$R^1$;

$R^1$ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

$R^2$ and $R^3$ are each independently hydrogen, halogen, optionally substituted alkyl, optionally substituted alkenyl, optionally substituted alkynyl, optionally substituted alkoxy, optionally substituted alkylthio, optionally substituted alkylsulfonyl, optionally substituted aminoalkyl, optionally substituted carbocyclic aryl, or optionally substituted aralkyl; and pharmaceutically acceptable sales thereof.

The pharmaceutical composition of the invention includes the analogs of formula I with the proviso that when $R^1$ is methyl, $R^2$ cannot be iodine or bromine and when $R^1$ is methyl, $R^2$ and $R^3$ cannot both be hydrogen.

Suitable halogen substitutent groups of compounds of Formula I as defined above (i.e. compounds of the invention) include F, Cl, Br and I. Cl is preferred. Alkyl groups of compounds of the invention typically have from 1 to about 12 carbon atoms, more preferably 1 to about 8 carbon atoms, still more preferably 1 to about 6 carbon atoms, even more preferably 1, 2, 3 or 4 carbon atoms, or still more preferably 1, 2 or 3 carbon atoms. As used herein, the term alkyl unless otherwise modified refers to both cyclic and noncyclic groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 12 carbon atoms, more preferably from 1 to about 8 carbon atoms, and still more preferably 1 to about 6 carbon atoms, even more preferably 1, 2, 3 or 4 carbon atoms. Preferred alkylthio groups of compounds of the invention include those groups having ore or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred. Preferred alkylsulfinyl groups of compounds of the invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred. Preferred aminoalkyl groups include those groups having more one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties. Suitable heteroaromatic groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazol. Suitable hereroalicyclic groups of compounds of the invention contain one or more N, O or S atoms and include, e.g., tetrahydrofuranyl, thienyl, tetrahydropyranyl, piperidinyl, morpholino and pyrrolindinyl groups. Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,5-substituted phenyl, 2,3,5-substituted and 2,4,5-substituted phenyl; and substituted naphthyl, including naphthyl substituted at the 5, 6 and/or 7 positions. Preferred substituents of such substituted carbocyclic groups are identified below.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—CH$_2$-naphthyl).

As discussed above, $R^1$, $R^2$, and $R^3$ groups of compound of the invention are optionally substituted. A "substituted" $R^1$, $R^2$, and $R^3$ group or other substituent may be substituted at one or more available positions, typically 1 to 3 or 4 positions, by one ore more suitable groups such as those disclosed herein. Suitable groups that may be present on a "substituted" $R^1$, $R^2$, and $R^3$ or other substitutent include e.g. halogen such as fluoro, chloro, bromo and iodo; cyano; hydroxyl; nitro, azido; alkanoyl such as a $C_{1-6}$ alkanoyl group such as acyl and the like; carboxamido; alkyl groups including those groups having 1 to about 12 carbon atoms or from 1 to about 6 carbon atoms and more preferably 1–3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl (e.g. an R group being a substituted or unsubstituted biphenyl moietyl); and aralkyl such as benzyl.

Preferred carbocyclic ring substituents of compounds of the invention incude halogen (F, Cl, Br and I; hydroxyl; azido; optionally substituted alkyl having 1 to about 6 carbons such as methyl, ethyl, propyl and butyl and branched groups such as isopropyl, sec-butyl and tert-butyl, and including haolgenated alkyl, particularly fluro-alkyl having 1 to about 6 carbon atoms; optionally substituted alkoxy having 1 to about 6 carbons such as methoxy, ethoxy, propoxy and butoxy, and including halogenated alkoxy, particularly fluro-alkoxy having 1 to about 6 carbon atoms; optionally substituted alkylthio having 1 to about 6 carbons such as methylthio and ethylthio; optionally substituted alkylsulfinyl having 1 to about 6 carbons such as methylsulfinyl) —S(O)CH$_3$) and ethylsulfinyl (—S(O) CH$_2$CH$_3$); and optionally substituted arylalkoxy such as benzyloxy (C$_6$H$_5$CH$_2$O—).

It should be understood that alkoxy, alkylthio, alkylsulfonyl and aminoalkyl substitutent groups described above include groups where a hetero atom is directly bonded to a ring system, such as a carbocyclic aryl group or a heterocyclic group, as well as groups where a hetero atom of the group is spaced from such ring system by an alkylene linkage, e.g. of 1 to about 4 carbon atoms.

Without wishing to be bound by theory, compounds of the invention that contain an alkylsulfonyl group, may be, in effect, "pro-drugs" wherein after administration of the compound to a subject the sulfinyl or sulfonyl group(s) are metabolized (reduced) in vivo to the corresponding sulfide moiety.

Depression states in which the present method is particularly useful in treating are those defined in the Diagnostic and Statistical Manual of Mental Disorders, third edition (DSM III), American Psychiatric Association, Washington, D.C. (1980), (DSM III, 296.2X to 296.6X and 301.13), including that characterized by anxiety or obsessional neuroses (DSM III, 300.40), or atypical depression (DSM III, 296.70 and 296.82), e.g., accompanied by a personality disorder. Other therapeutic uses for the method include treatment of post-traumatic stress disorder (DSM III, 308.30 and 309.81), obsessive compulsive behavioral states (DSM III, 300.-30), anxiety states (DSM III, 300.00, 300.01, 300.02, 300.21, 300.22, 300.23 and 300.29), e.g., which are accompanied in an acute phase by panic attacks with or without phobia (DSM III 300.21), phobia (DSM III 300.23 and 300.29), appetite disorders, e.g., bulimia (DSM IIII, 307.51) and anorexia (DSM III, 307.10), and borderline personality disorder (DSM IIII, 301.83) in human beings identified as having such disorders. Still further therapeutic uses for the method include treatment of headaches, e.g. migraine, muscle contraction and mixed (i.e., combination of migraine and muscle contraction) headaches in human beings having such headaches.

5-MCA-NAT and its analogs may be administered by, for example, the oral, rectal, transdermal or parenteral route. In general, the compound may be administered for the treatment of each of the disorders stated herein above, including depression, in the dosage range of 0.01 mg/kg to 500 mg/kg of human body weight per day, preferably about 0.1 mg/kg to about 50 mg/kg of human body weight per day and optimally about 10 mg/kg of human body weight per day. The precise dosage will naturally depend on a number of clinical factors, for example, the age of the recipient, the route of administration and the condition under treatment and its severity: for administration of 5-MCA-NAT by the oral route, a dosage regime of 0.05 mg/kg per day to 50 mg/kg per day, preferably 5 mg/kg per day to 25 mg/kg per day and optimally about 10 mg/kg per day, may be used. The desired daily dose is preferably given as two or three or more subdoses administered at appropriate intervals during the day.

While it is possible to administer 5-MCA-NAT and its analogs as the raw chemical, it is highly desirable to administer it in the form of a pharmaceutical formulation comprising 5-MCA-NAT and its analogs together with an acceptable carrier therefor; the carrier should be acceptable in the sense of being compatible with the other ingredients and not deleterious to the recipient thereof. The formulations may be adapted for oral, transdermal, parenteral or rectal administration.

The formulations may conveniently be presented in unit dosage form and may be prepared by any methods well known in the art of pharmacy. Such methods include the step of bringing into association the active ingredient with the carrier which may comprise one or more accessory ingredients. In general the formulations are prepared by uniformly and intimately bringing into association the active ingredient with liquid carriers or finely divided solid carriers or both, and then, if necessary, shaping or encapsulating the product.

Formulations suitable for oral administration may be presented in discrete units such as capsules, cachets or tablets each containing a predetermined amount of active ingredient; as a powder or granules; as a solution or a suspension in an aqueous liquid or a non-aqueous liquid; or as an oil-in-water liquid emulsion or a water-in-oil liquid emulsion.

A tablet may be made by compression or molding, optionally with one or more accessory ingredients. Compressed tablets may be prepared by compressing in a suitable machine the active ingredient in a free-flowing form such as a powder of granules, optionally mixed with a binder, lubricant, inert diluent, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for rectal administration may be presented as a suppository with the usual carriers such as cocoa butter.

Formulations suitable for parenteral administration include aqueous sterile injection solutions which may contain antioxidants, buffers, bacteriostats and solutes which renders the formulation isotonic with the blood of the intended recipient; and aqueous and non-aqueous sterile suspensions which may include suspending agents and thickening agents. The formulations may be presented in unit doses or multidose containers, for example, sealed ampoules and vials, and may be stored in a freeze dried (luophilized) condition requiring only the addition of the sterile liquid carrier, for example, PEG 400: ethanol mixtures, immediately prior to use. Extemporaneous injection solutions and suspensions may be prepared from sterile powders, granules and tablets of the kind previously described.

Preferred unit dosage formulations are those containing a daily subdose, as herein above recited, or an appropriate fraction thereof, of the active ingredient.

It should be understood that in addition to the ingredients particularly mentioned above, the formulations of this invention may include other agents conventional in the art having regard to the type of formulation in question, for example, those suitable for oral administration may include flavoring agents.

5-MCA-NAT and its analogs may be prepared by those methods known in the art or purchased commercially from, for example, Tocris or Sigma Chemical Company, catalogued as GR135531.

5-MCA-NAT and its analogs may be administered alone or in combination with other therapeutically effective agents, for example, antidepressants such as nortriptyline, MAO-inhibitors and serotonin reuptake inhibitors. Use of 5-MCA-NAT and its analogs in combination with other drugs used presently in treating depression, may reduce the amounts of drugs used in the treatment and thereby alleviating some of the major side effects observed. Furthermore, the period observed between administering the drugs and any observed therapeutic indications may be diminished.

Additionally, the present inventors have found that, unexpectedly, the antidepressant action of 5-MCA-NAT is potentiated by the $Ca^{++}$ antagonist, Nifedipine. Accordingly, 5-MCA-NAT and its analogs may be combined with a $Ca^{++}$ antagonist. Nifedipine is a preferred antagonist.

The present invention is further illustrated by the following Example. The Example is provided to aid in the understanding of the invention and is not to be construed as a limitation thereof.

EXAMPLE

In the present study, the tail suspension test in C57BL/6J mice was used to evaluate 5-MCA-NAT antidepressant-like activity. The tail suspension test is a variant of the "behavioral despair" forced swimming test in which immobility is induced by suspending an animal by the tail (Steru et al., 1985). Unlike forced swimming, tail suspension-induced immobility is not accompanied by marked hypothermia or behavioral changes lasting longer than the test period itself, suggesting that the procedure is less stressful to the experimental animals. Although most of the clinically active antidepressants revealed antidepressant-like activity in both tests, some antidepressants are more active in tail suspension (e.g., selective serotonin uptake inhibitors) than in the forced swimming test (e.g., MAO inhibitors) (for review see Porsoult et al., 1993).

Materials and Methods

C57BL/6 mice (birth weight 21–25 g) were housed, ten per cage, in light controlled chambers (12 hr. light/12 hr. dark cycle—lights on at 08.00 hr., off at 20.00 hr.) with free access to food and water. Each animal was tested in a chamber made out of white non-transparent plastics. The C57BL/6J mice are suitable animals for such a study since no enzymes of melatonin biosynthesis have been found in the pineal glands of this strain of mice (Ebihara et al., 1986). Therefore, the observed effects could not be attributed to melatonin.

The chamber was 17 cm W×25 cm H×15 cm D with a hook (4 cm) attached to the center of the ceiling. There was no front wall to allow for the observation of the mouse behavior. The mouse was hung on a hook by an adhesive tape placed 15 mm from the extremity of its tail. The animal was positioned with its stomach towards the investigator to assure the observation of the total immobility. The distance between the floor of the chamber and the nose of the animal was 10 cm. Immobility was scored as a sum of the time periods during which the animal hung passively and motionless for at least 2 sec. The total period of observation was 6 min. Experiments were conducted between 10.00 hr. and 14.00 hr. in a quiet room. The source of the light (50 W fluorescent bulb) was positioned 2 m above the experimental chamber. Baseline, control experiments were conducted several days before the actual experiments. Only those animals whose cumulative duration of immobility during the 6 min. observation was no less than 100 sec. were selected for further experiments.

Three animals were tested simultaneously. Each experimental group was composed of at least nine animals. The drugs were dissolved in saline/twin (10%) solutions and administered intra-peritoneally (i.p.) at doses ranging from 5 mg/kg to 50 mg/kg. 5-MCA-NAT (from Tocris) was administered 30 min. before the testing. All control animals were injected with the vehicle and evaluated on the same day as the animals injected with the experimental drugs. 5-MCA-NAT was injected 15 min. before nifedipine in a dose (10 mg/kg i.p.) which, by itself has no effect on the duration of immobility FIG. 1). Nifedipine, a $Ca^{++}$ antagonist, was injected 15 min. after the 5-MCA-NAT. Nifedipine was injected in a dose (5 mg/kg, i.p.) which, by itself, has no effect on the duration of immobility (Prakhie and Oxenkrug, 1998). Prazocin, MT-3 antagonist (Marco et al., 1999) was injected 15 min. before 5-MCA-Nat (50 mg/kg) in a dose (0.5 mg/kg) which by itself has no effect on the duration of immobility. Results were expressed as mean ±S.D. (sec.) and statistically treated by ANOVA and Student t-test.

Results

The results, shown in FIG. 1, demonstrate that 5-MCA-NAT decreased the duration of immobility. The effect was dose dependent: low dose of 5-MCA-Nat (10 mg/kg) did not affect the duration of immobility while higher doses (25, and 50 mg/kg) decreased the duration of immobility, i.e., revealed the antidepressant-like activity (FIG. 1).

Nifedipine (5 mg/kg) did not affect the duration of immobility. The combination of ineffective doses of nifedipine (5 mg/kg) and 5-MCA-NAT (10 mg/kg) decreased the duration of immobility.

Figure 2:
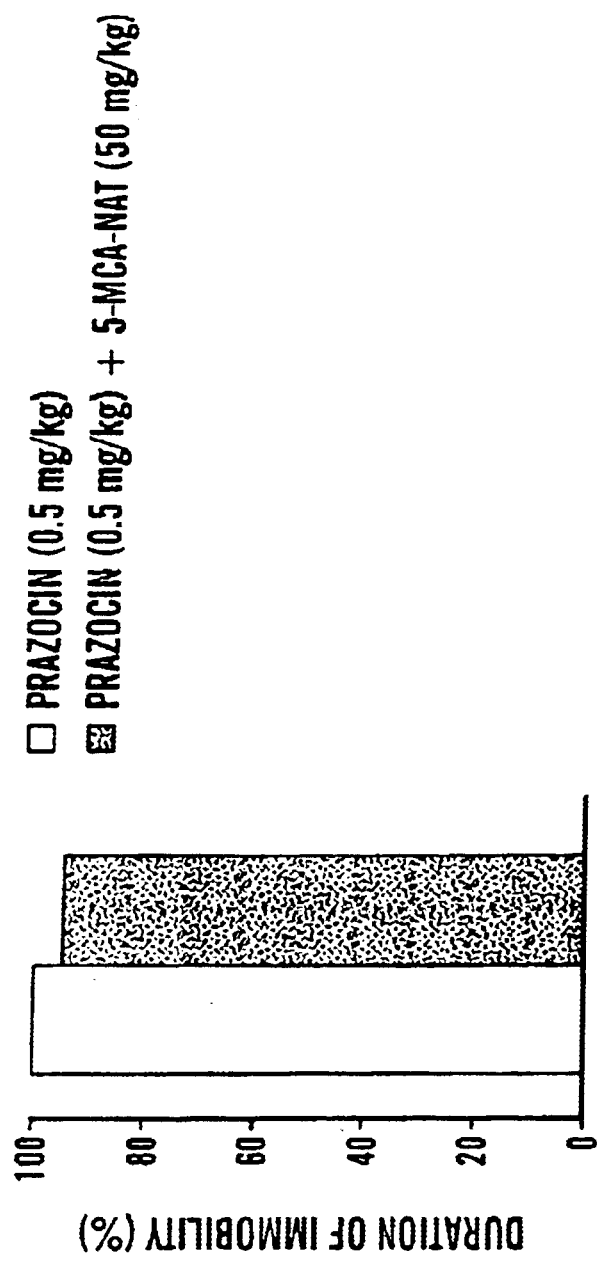
FIG. 2 is a graph showing the results of using prazocin alone and in combination with 5-MCA-NAT in the mouse tail suspension test.

Prazocin (0.5 mg/kg) did not affect the duration of immobility, but prevented decrease of immobility, induced by 5-MCA-NAT (50 mg/kg) (FIG. 2).

The mean duration of immobility for all control groups combined was 212.78±27.75 sec. (mean±S.D.).

Discussion

The results indicated that 5-MCA-NAT has antidepressant-like activity (decreased duration of immobility) in the tail suspension test. To the best of our knowledge, this is the first observation of the antidepressant-like activity of 5-MCA-NAT. The mechanism of the 5-MCA-NAT antidepressant-like activity revealed by the tail suspension test is most likely, mediated by the stimulation of MT-3 receptors since MT-3 antagonist, prazocin, completely prevented the effect of 5-MCA-NAT. The recent revision of the nomenclature and classification of melatonin receptors recognizes three types of melatonin receptor: mt-1, MT-2 and MT-3 (Marco et al., 1999). 5-MCA-NAT is a ligand to the MT-3 melatonin receptor (Dubocovich M. L. *Trends Pharmacol. Sci.*, 1995, 16:50–56). Melatonin is of considerable interest for its circadian regulation of a variety of physiological and neuroendocrine processes, most notably in its role in modulating circadian rhythms and for its antidepressant activities. The melatonin receptor MT-3 agonist, 5-MCA-NAT may function via the same mechanism as melatonin once bound to the MT-3 receptor. Other MT-3 agonists might also have an antidepressant effect similar to 5-MCA-NAT.

We have also found that 5-MCA-NAT acted synergistically with nifedipine, the $Ca^{++}$ antagonist, which potentiated the antidepressant-like activity of 5-MCA-NAT. The antidepressant-like effect of MT-3 agonists might be potentiated by $Ca^{++}$ antagonists like, for example, nifedipine. Calcium involvement in pineal function has been shown previously (Morton and Reiter, 1991). The possibility of antidepressant action of nifedipine and other $Ca^{++}$ antagonists has been discussed elsewhere (Kozlovskii and Prahie, 1994). Further investigation of the mechanism of the 5-MCA-NAT antidepressant-like activity and its synergism with nifedipine is needed.

The following references are cited throughout the specification. All documents mentioned herein are incorporated herein by reference.

Dubocovich M. L. (1983). Melatonin is a potent modulator of dopamine release in the retina. *Nature*, 306:782–784.

Dubocovich M. L. (1984). N-Acetyltryptamine antagonizes the melatonin-induced inhibition of [$^3$H] dopamine release from retina. *Eur. J. Pharmacol.*, 105:193–194.

Dubocovich M. L. (1985). Characterization of a retinal melatonin receptor. *J. Pharmacol. Exp. Ther.*, 234:395–401.

Dubocovich M. L., and J. S. Takahashi. (1987). Use of 2-[$^{125}$I]iodomelatonin to characterize melatonin binding sites in chicken retina. *Proc. Nat'l. Acad. Scl. U.S.A.*, 84:3916–3920.

Dubocovich M. L. (1995). Melatonin receptors: are there multiple subtypes. *Trends Pharmacol. Sci.*, 16:50–56.

Duncan M. J., Takahashi J. S., and M. L. Dubocovich. (1989). Characteristics and autoradiographic localization of 2-[$^{125}$I]iodomelatonin binding sites in Djungarian hamster brain. *Endocrinol.*, 125:1011–1018.

Ebihara S., Marks T., Hudson D. J., and M. Menaker (1986). Genetic control of melatonin synthesis in the pineal gland of the mouse. *Science*, 231: 491–493.

Jensen P. S., Bhatara V. S., Vitiello B., Hoagwood K., Feil M., and L. B. Burke. (1999). Psychoactive medication prescribing practices for U.S. children: gaps between research and clinical practice. *Child and Adolescent Research* 38(5):557–565.

Kozlovski V L and I V Prahie (1994). Calcium channel blockers as antidepressants—a property of the class or the individual preparation? *Experimental and Clinical Pharmacology* (Russian), 57: 17–20.

Marco M, Vincenzo P P, Gilberto S, Giorgio T. Melatonin. Current Medical Chemistry, 1999; 6: 501–518.

Mollinari E. J., North P. C., and M. L. Dubocovich. (1994). Localization and characterization of $ML_2$ binding sites with 2-[$^{125}$I]-MCA-NAT to CNS and peripheral tissues of various species. *Soc. Neurosci. Abstr.*, 20:1168.

Morton D. J., and R. J. Reiter (1991) Involvement of calcium in pineal gland function. *Proc. Soc. Exper. Biol. Med.*, 197: 378–383.

Pache P. (1999). Speculations on the differences between tricyclic and selective serotonin reuptake inhibitor antidepressants on their cardiac effects. Is there any? *Curr. Med. Chem.* 6(6):469–480.

Poursolt, R. D. (1987) The automated tail suspension test: a computerized device which differentiates psychotropic drugs. *Prog. NeuroPsychopharmacol & Biol Psychiat.*, 11:659–673.

Poursolt R. D., McArthur R. A., and A. Lenegre. (1993) Psychotropic Screening Procedures. In Models in Behavioral Pharmacology (F. van Haaren—Ed), Elsevier Science Publishers, pp: 23–50.

What is claimed is:

1. A pharmaceutical composition comprising an MT-3 agonist of the following formula I:

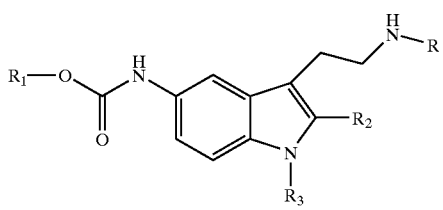

wherein

R is —S(O)$_2$R$_1$ or S(O)R$_1$,

R$_1$ is optionally substituted alkyl; optionally substituted alkoxy; optionally substituted aminoalkyl; optionally substituted carbocyclic aryl; an optionally substituted alkylaryl;

R$_2$ is hydrogen, halogen, optionally substituted alkyl, optionally substituted alkenyl, optionally substituted alkynyl, optionally substituted alkoxy, optionally substituted alkylthio, optionally substituted alkylsulfonyl, optionally substituted aminoalkyl; and pharmaceutically acceptable salts thereof, R$_3$ is hydrogen, halogen, optionally substituted alkyl, optionally substituted alkenyl, optionally substituted alkynyl, optionally substituted alkoxy, optionally substituted alkylthio, optionally substituted alkylsulfonyl, optionally substituted aminoalkyl, optionally substituted carbocyclic aryl, or optionally substituted aralkyl; and pharmaceutically acceptable salts thereof, wherein the optional substituents, which may be at one or more available positions, are selected from the group consisting of halogen, cyano, hydroxyl, nitro, azido, C$_{1-6}$ alkanoyl, carboxamido, alkyl, alkenyl, alkynyl, alkoxy, alkylthio, alkylsulfinyl, alkylsulfonyl and aminoalkyl with the proviso that when R$_1$ is methyl, R$_2$ cannot be iodine or bromine and when R$_1$ is methyl, R$_2$ and R$_3$ cannot both be hydrogen and a pharmaceutically acceptable carrier.

2. The pharmaceutical composition of claim 1, further comprising a Ca$^{++}$ antagonist.

3. The pharmaceutical composition of claim 2, wherein the Ca$^{++}$ antagonist is nifedipine.

4. The pharmaceutical composition of claim 3 further comprising an acceptable carrier.

5. The pharmaceutical composition of claim 1, wherein R$_1$ is optionally substituted C$_{1-6}$ alkyl or optionally substituted C$_{1-6}$ alkoxy.

6. The pharmaceutical composition of claim 1, wherein R$_2$ and R$_3$ are each independently halogen, optionally substituted C$_{1-6}$ alkyl, optionally substituted C$_{1-6}$ alkoxy, or optionally substituted C$_{1-6}$ alkythio.

7. The pharmaceutical composition of claim 1 further comprising an acceptable carrier.

* * * * *